United States Patent [19]

Berg et al.

[11] Patent Number: 4,693,789

[45] Date of Patent: * Sep. 15, 1987

[54] SEPARATION OF ISOPROPYL ACETATE FROM ISOPROPANOL BY EXTRACTIVE DISTILLATION

[76] Inventors: Lloyd Berg; An-I Yeh, both of 1314 S. Third Ave., Bozeman, Mont. 59715

[*] Notice: The portion of the term of this patent subsequent to Jun. 25, 2002 has been disclaimed.

[21] Appl. No.: 836,488

[22] Filed: Mar. 5, 1986

[51] Int. Cl.$^4$ .......................... B01D 3/40; C07C 67/48
[52] U.S. Cl. ........................................ 203/51; 203/56; 203/58; 203/59; 203/63; 560/248
[58] Field of Search .......................... 203/59, 58, 63, 51, 203/56, 18, 14, 19; 560/248, 234; 568/913, 918

[56] References Cited

U.S. PATENT DOCUMENTS

| | | | |
|---|---|---|---|
| 1,770,414 | 7/1930 | Martin et al. | 560/234 |
| 2,489,619 | 11/1949 | Carlson et al. | 203/63 |
| 2,575,285 | 11/1951 | Carlson et al. | 203/63 |
| 2,822,409 | 2/1958 | Gwynn et al. | 568/913 |

FOREIGN PATENT DOCUMENTS

| | | | |
|---|---|---|---|
| 1089744 | 9/1960 | Fed. Rep. of Germany | 203/64 |
| 54-46701 | 4/1979 | Japan | 560/248 |

*Primary Examiner*—Wilbur Bascomb

[57] ABSTRACT

Isopropyl acetate cannot be completely removed from isopropyl acetate - isopropanol - water mixtures by distillation because of the presence of the minimum ternary azeotrope. Isopropyl acetate can be readily removed from mixtures containing it, isopropanol and water by using extractive distillation in which the extractive agent is a higher boiling oxygenated or nitrogenous organic compound or a mixture of these. Typical examples of effective agents are diethanolamine; ethanolamine and N-methyl pyrrolidone; triethanolamine and N-methyl pyrrolidone.

9 Claims, No Drawings

SEPARATION OF ISOPROPYL ACETATE FROM ISOPROPANOL BY EXTRACTIVE DISTILLATION

DUAL APPLICATIONS

This application is related to Application Ser. No. 768,330, filed Aug. 22, 1985.

FIELD OF THE INVENTION

This invention relates to a method for separating isopropyl acetate from isopropanol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the most volatile component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

One of the commercially important ways to manufacture isopropyl acetate is by the catalytic esterification of isopropanol with acetic acid. Isopropyl acetate (b.p.=88.7° C.), isopropanol (b.p.=82.3° C.) and water (b.p.=100° C.) form a ternary azeotrope boiling at 75.5° C. containing 76 wt.% isopropyl acetate, 13 wt.% isopropanol and 11 wt.% water. Isopropyl acetate also forms a binary azeotrope with isopropanol which boils at 80.1° C. and contains 47.4 wt.% isopropyl acetate and a binary azeotrope with water boiling at 75.9° C. containing 88.9 wt.% isopropyl acetate. Isopropanol also forms a binary minimum azeotrope with water which boils at 80.4° C. and contains 87.8 wt.% isopropanol. Thus in the esterification of isopropanol with acetic acid to form isopropyl acetate and water, the rectification of this mixture has three binary and one ternary azeotrope to contend with, and yields the lowest boiling constituent, namely the isopropyl acetate-isopropanol-water ternary azeotrope. It is therefore impossible to produce isopropyl acetate from isopropanol and water mixtures by rectification because the lower boiling ternary azeotrope will always come off overhead as the initial product. Any mixture of isopropyl acetate, isopropanol and water subjected to rectification at one atmosphere pressure will produce an overhead product boiling at 75.5° C. and containing 76 wt.% isopropyl acetate, 13 wt.% isopropanol and 11 wt.% water. Extractive distillation would be an attractive method of effecting the separation of isopropyl acetate from isopropanol if agents can be found that (1) will break the isopropyl acetate-isopropanol-water azeotrope and (2) are easy to recover from the isopropanol, that is, form no azeotrope with isopropanol and boil sufficiently above isopropanol to make the separation by rectification possible with only a few theoretical plates.

Extractive distillation typically requires the addition of an equal amount to twice as much extractive agent as the isopropyl acetate-isopropanol-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is to be done by azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with isopropanol otherwise it will form a two-phase azeotrope with isopropanol in the recovery column and some other method of separation will have to be employed.

The breaking of this azeotrope by extractive distillation is a new concept. The closest application of the concept might be the breaking of the methyl acetate-methanol azeotrope reported by Yoshida & Oka in Japanese Pat. No. 54/119-411, Sept. 17, 1979, the breaking of the acetone-methanol azeotrope reported by Berg & Yeh, U.S. Pat. No. 4,501,645, Feb. 26, 1985 or the breaking of the n-butyl acetate-n-butanol-water azeotrope reported by Berg & Yeh, U.S. Pat. No. 4,525,245, June 26, 1985.

OBJECTIVE OF THE INVENTION

The object of this invention is to provide a process or method of extractive distillation that will enhance the relative volatility of isopropyl acetate from isopropanol in their separation in a rectification column. It is a further object of this invention to identify suitable extractive distillation agents which will eliminate the isopropyl acetate-isopropanol-water ternary azeotrope and make possible the production of pure isopropyl acetate and isopropanol by rectification. It is a further object of this invention to identify organic compounds which, in addition to the above constraints, are stable, can be separated from isopropanol by rectification with relatively few theoretical plates and can be recycled to the extractive distillation column and reused with little decomposition.

SUMMARY OF THE INVENTION

The object of the invention is provided by a process for separating isopropyl acetate from isopropanol which entails the use of certain amino alcohols as the agents in extractive distillation.

DETAILED DESCRIPTION OF THE INVENTION

We have discovered that certain amino alcohols, both individually and as mixtures, will effectively negate the isopropyl acetate-isopropanol-water ternary azeotrope and permit the separation of pure isopropyl acetate from isopropanol by rectification when employed as the agent in extractive distillation. Table 1 lists several amino alcohols and their mixtures and approximate proportions that we have found to be effective. The data in Table 1 was obtained in a vapor-liquid equilibrium still. In each case, the starting material was the isopropyl acetate-isopropanol-water azeotrope. The ratios are the parts by weight of extractive agent used per part of isopropyl acetate-isopropanol-water azeotrope. The relative volatilities are listed for each when two ratios were employed. The compounds that are effective when used alone are ethanolamine, diethanolamine, triethanolamine, N-methyl ethanol-amine, methyl diethanolamine and isopropanolamine. The compound which is effective when used in mixtures with amino alcohols is N-methyl-pyrrolidone. The two relative volatilities shown in Table 1 correspond to the two different ratios employed. For example, in Table 1, one half

TABLE 1

Effective Agents For Separating Isopropyl Acetate From Isopropanol Which Contain Amino Alcohols

| Compound | Ratios | Relative Volatilities |
| --- | --- | --- |
| Ethanolamine | 1 | 3.54 |
| Diethanolamine | " | 2.72 |
| Triethanolamine | " | 2.03 |
| N—Methyl ethanolamine | " | 2.31 |
| Methyl diethanolamine | " | 6/5 1.46 1.88 |
| Isopropanolamine | " | 2.48 |
| Ethanolamine, N—Methylpyrrolidone | $(\frac{1}{2})^2$ | 3.22 |
| Triethanolamine, N—Methyl pyrrolidone | " | $(3/5)^2$ 1.98 1.99 | part of N-methylpyrrolidone mixed with one half part of triethanolamine with one part of the isopropyl acetate-isopropanol-water azeotrope gives a relative volatility of 1.98, 3/5 parts of N-methylpyrrolidone plus 3/5 parts of triethanolamine gives 1.99. In every example in Table 1 the starting material is the isopropyl acetate-isopropanol-water azeotrope which possesses a relative volatility of 1.0.

TABLE 2

Data From Run Made In Rectification Column

| Agent | Wt. % Isopropyl Acetate Overhead | Bottoms | Relative Volatility |
| --- | --- | --- | --- |
| Blank | 84.6 | 82.6 | 1.03 |
| Ethanolamine | 98 | 83.8 | 3.4 |

Initial Mixture: 304 gm. Isopropyl acetate + 52 gm. Isopropanol + 44 gm. Water
Blank: No agent used
Agent Added at 20 ml/min. and 65° C.

The data in Table 2 was obtained in the following manner. The charge was 76 wt.% isopropyl acetate, 13 wt.% isopropanol and 11 wt.% water and after a half hour of operation in the 4.5 theoretical plate column to establish equilibrium, ethanolamine at 65° C. and 20 ml/min. was pumped in. The rectification was continued for two hours with sampling of overhead and bottoms after one hour, 1.5 hours and two hours. The average of the three analyses was 98 wt.% isopropyl acetate in the overhead and 83.8 wt.% in the bottoms, both on a water-free basis which gives a relative volatility of 3.4 of isopropyl acetate to isopropanol. This indicates that the ternary azeotrope has been negated and separation accomplished. The isopropyl acetate comes off in the form of its binary azeotrope with water which on condensation, immediately forms two liquid layers. The solubility of isopropyl acetate in water is only 3%.

THE USEFULNESS OF THE INVENTION

The usefulness or utility of this invention can be demonstrated by referring to the data presented in Tables 1 & 2. All of the successful extractive distillation agents show that isopropyl acetate, isopropanol and water can be separated from their ternary azeotrope by means of distillation in a rectification column and that the ease of separation as measured by relative volatility is considerable. Without these extractive distillation agents, no improvement above the azeotrope composition will occur in a rectification column. The data also show that the most attractive agents will operate at a boilup rate low enough to make this a useful and efficient method of recovering high purity isopropyl acetate from any mixture of these three including the ternary minimum azeotrope. The stability of the compounds used and the boiling point difference is such that complete recovery is obtainable by a simple distillation and the amount required for make-up is small.

WORKING EXAMPLES

Example 1

The isopropyl acetate-isopropanol-water azeotrope is 76 wt.% isopropyl acetate, 13 wt.% isopropanol, 11 wt.% water. Fifty grams of the isopropyl acetate-isopropanol-water azeotrope and fifty grams of methyl diethanolamine were charged to an Othmer type glass vapor-liquid equilibrium still and refluxed for eleven hours. Analyses of the vapor and liquid by gas chromatography gave vapor composition of 83.4% isopropyl acetate, 16.6% isopropanol; liquid composition of 77.5% isopropyl acetate, 22.5% isopropanol. This indicates a relative volatility of 1.46. Ten grams of methyl diethanolamine were added and refluxing continued for another twelve hours. Analyses gave vapor composition of 83.2% isopropyl acetate, 16.8% isopropanol; liquid composition of 72.6% isopropyl acetate, 27.4% isopropanol which is a relative volatility of 1.88.

Example 2

Fifty grams of the isopropyl acetate-isopropanol-water azeotrope, 25 grams of N-methyl pyrrolidone and 25 grams of triethanolamine were charged to the vapor liquid equilibrium still and refluxed for nine hours. Analyses indicated a vapor composition of 90.7% isopropyl acetate, 9.3% isopropanol; a liquid composition of 83.2% isopropyl acetate, 16.8% isopropanol which is a relative volatility of 1.98. Five grams of N-methyl pyrrolidone and five grams of triethanolamine were added and refluxing continued for another twelve hours. Analyses indicated a vapor composition of 90.2% isopropyl acetate, 9.8% isopropanol; a liquid composition of 82.2% isopropyl acetate, 17.8% isopropanol which is a relative volatility of 1.99.

Example 3

A glass perforated plate rectification column was calibrated with ethylbenzene and p-xylene which possesses a relative volatility of 1.06 and found to have 4.5 theoretical plates. A solution of 304 grams of isopropyl acetate, 52 grams of isopropanol and 44 grams of water was placed in the stillpot and heated. When refluxing began, an extractive agent comprising ethanolamine was pumped into the column at a rate of 20 ml/min. The temperature of the extractive agent as it entered the column was 65° C. After establishing the feed rate of the extractive agent, the heat input to the isopropyl acetate, isopropanol and water in the stillpot was adjusted to give a total reflux of 10–20 ml./min. After one hour of operation, the overhead and bottoms samples of approximately two ml. were collected and analysed by gas chromatography. The overhead analyses were 98% isopropyl acetate, 2% isopropanol. The bottoms analyses were 83.8% isopropyl acetate, 16.2% isopropanol. Using these compositions in the Fenske equation, with the number of theoretical plates in the column being 4.5, gave an average relative volatility of 3.4 for each theoretical plate.

We claim:

1. A method for recovering isopropyl acetate from a mixture of isopropyl acetate, isopropanol and water which comprises distilling a mixture of isopropyl acetate, isopropanol and water in a rectification column in the presence of about one to two parts of an extractive agent per part of isopropyl acetate-isopropanol-water mixture, recovering isopropyl acetate and water as overhead product and obtaining the extractive agent and isopropanol from the stillpot, the extractive agent comprises at least one amino alcohol containing from two to six carbon atoms.

2. The method of claim 1 in which the extractive agent comprises ethanolamine.

3. The method of claim 1 in which the extractive agent comprises diethanolamine.

4. The method of claim 1 in which the extractive agent comprises triethanolamine.

5. The method of claim 1 in which the extractive agent comprises N-methyl ethanolamine.

6. The method of claim 1 in which the extractive agent comprises methyl diethanolamine.

7. The method of claim 1 in which the extractive agent comprises isopropanolamine.

8. The method of claim 1 in which the extractive agent comprises a mixture of ethanolamine and N-methyl pyrrolidone.

9. The method of claim 1 in which the extractive agent comprises a mixture of triethanolamine and N-methyl pyrrolidone.

* * * * *